(12) United States Patent
Yokoi et al.

(10) Patent No.: US 7,244,229 B2
(45) Date of Patent: Jul. 17, 2007

(54) CAPSULE ENDOSCOPE

(75) Inventors: Takeshi Yokoi, Hino (JP); Akira Hasegawa, Musashino (JP); Shinya Matsumoto, Machida (JP); Takayuki Suzuki, Hachioji (JP); Hidetake Segawa, Hachioji (JP); Hironobu Takizawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/200,129

(22) Filed: Aug. 10, 2005

(65) Prior Publication Data
US 2005/0288557 A1    Dec. 29, 2005

Related U.S. Application Data

(62) Division of application No. 10/347,325, filed on Jan. 21, 2003, now Pat. No. 6,939,295.

(30) Foreign Application Priority Data
Mar. 8, 2002    (JP)    ............................. 2002-064018

(51) Int. Cl.
*A61B 1/05*    (2006.01)
(52) U.S. Cl. ..................... 600/176; 600/160; 600/167
(58) Field of Classification Search ................ 600/176, 600/160, 167, 129; 359/725, 724, 728
See application file for complete search history.

(56) References Cited

U.S. PATENT DOCUMENTS 4,864,137 A * 9/1989 Klein ........................ 250/343
4,932,764 A * 6/1990 Simpson, Jr. ............... 359/725
5,951,464 A * 9/1999 Takahashi et al. .......... 600/176
6,038,079 A * 3/2000 Michaels .................... 359/661
6,134,056 A * 10/2000 Nakamuka ................... 359/784
2003/0158503 A1* 8/2003 Matsumoto ................. 600/593

FOREIGN PATENT DOCUMENTS

| JP | 2001-91860 | 4/2001 |
| WO | WO 00/76391 A1 | 12/2000 |
| WO | WO 01/65995 A2 | 9/2001 |

* cited by examiner

*Primary Examiner*—John P. Leubecker
(74) *Attorney, Agent, or Firm*—Arnold International; Bruce Y. Arnold

(57)    ABSTRACT

A capsule endoscope is disclosed having an illumination means, an imaging system that includes an objective optical system, and a transparent cover. The invention is characterized by one of: (1) the transparent cover has a larger radius of curvature in a central region of the field of view of the objective optical system than the radius of curvature of the transparent cover in a peripheral region of the field of view of the objective optical system, or (2) the imaging system has a different near point of focus distance for a central region of the field of view than the near point of focus distance of a region that is peripheral to the central region of the field of view and the objective optical system includes a meniscus lens element of positive refractive power and a plano-convex lens element.

6 Claims, 4 Drawing Sheets

CAPSULE ENDOSCOPE

CROSS-REFERENCE TO RELATED APPLICATION

This is a divisional application of allowed U.S. application Ser. No. 10/347,325, filed Jan. 21, 2003, now U.S. Pat. No. 6,939,295, issued on Sep. 6, 2005.

BACKGROUND OF THE INVENTION

In recent years, endoscopes have come to be widely used in both the medical field and in industry. Recently, endoscopes have been developed which do not require an inserted part and which avoid the pain associated with inserting an insertion part. In these endoscopes that are used in the medical field, a patient swallows an endoscope which has been miniaturized and placed within a capsule. For example, see Japanese Laid Open Patent Application No. 2001-91860 and published PCT application WO 01/65995 A2.

In the above-mentioned patent application, an objective lens and an illumination means formed of a luminescent diode are installed inside a near-hemispherical transparent cover. An object to be observed is illuminated by a luminescent diode and an objective lens forms an image of the object on an image sensor. The objective lens has a configuration wherein lens elements of positive and negative refractive power are combined to form a joined lens, and there is no disclosure about the depth of field of the objective optical system. The image sensor is of the CMOS type, and the objective lens consists of a biconvex lens element, and there is no disclosure about the depth of field of the objective optical system.

In these conventional examples, because an objective lens and an illumination body are fixed inside a near-hemispherical transparent cover and the curvature radius is the same between the central region of the field of view and the peripheral region of the field of view, there was an inconvenience in that the mucosa layer easily contacts the central region of the transparent cover, causing an obstruction in the field of view of the central region. Also, when the transparent front cover has a single radius of curvature (i.e., one defined by one-half the outer diameter of the capsule that is fitted to the transparent cover), the outer diameter of the capsule becomes excessive, making the capsule difficult to swallow and giving it low motility when within the body.

BRIEF SUMMARY OF THE INVENTION

The present invention relates to a capsule endoscope that is swallowed in order to examine the interior of a living body. A first object of the invention is to provide a capsule endoscope which can miniaturize the capsule size and thus improve the ease with which it may be swallowed while ensuring a sufficient field of view for observation. A second object of the invention is to provide a capsule endoscope which provides good images over the entire field of view without increasing the total length of the capsule. A third object of the invention is to provide a capsule endoscope wherein the near point distance is made larger in a central region of the field of view than in a region of the field of view that is peripheral to the cental region. This enables deeper regions to be imaged in focus in the central region of the field of view. Since the field of view in peripheral regions is typically obscured by a nearby cavity wall as the capsule endoscope passes within a cavity of a patient, making the near point of focus deeper in the central region does not otherwise degrade the imaging performance of the capsule endoscope.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

The present invention is a capsule endoscope having an illumination means, an imaging system that includes an objective optical system, and a transparent cover. The invention is characterized by one of: (1) the transparent cover has a larger fixed radius of curvature in a central region of the field of view of the objective optical system than the radius of curvature of the transparent cover in a peripheral region of the field of view of the objective optical system, or (2) the imaging system has a different near point of focus distance for a central region of the field of view than the near point of focus distance of a region that is peripheral to the central region of the field of view.

Several embodiments of the invention will now be discussed in detail with reference to the drawings.

EMBODIMENT 1

Figures 1A, 1B:
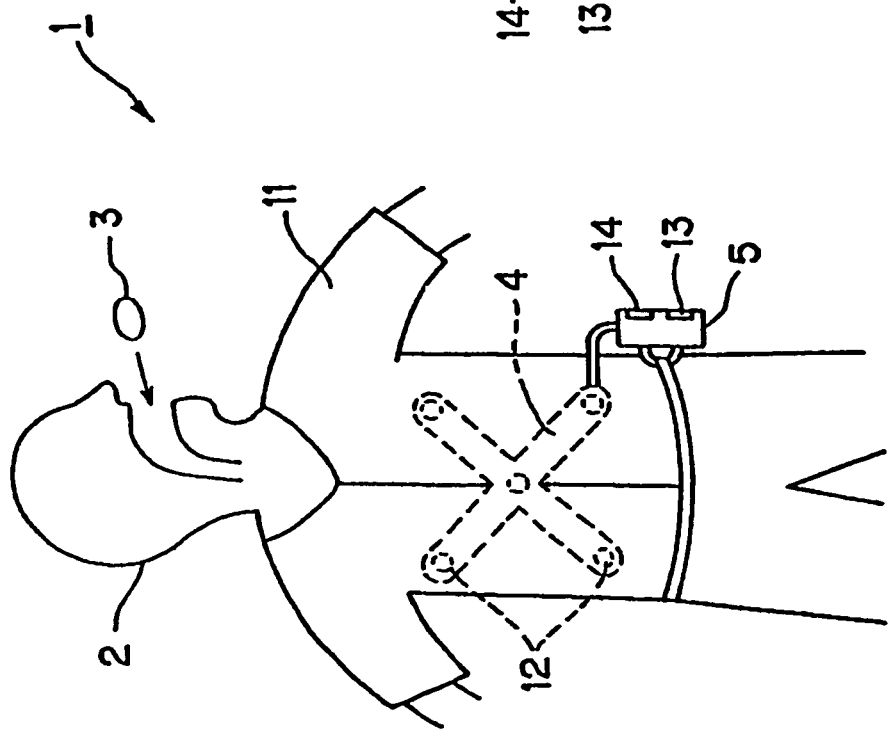
FIGS. 1(A) and 1(B) show a capsule endoscope system according to the invention.

Embodiment 1 will be described with reference to FIGS. 1(A), 1(B) and 2. FIGS. 1(A) and 1(B) show the capsule endoscope system, with FIG. 2 being a cross-sectional view showing the internal configuration of the capsule endoscope according to this embodiment. As shown in FIG. 1(A), a capsule endoscope apparatus 1 which is equipped with the first embodiment for performing endoscopic examinations uses a capsule endoscope 3 which wirelessly transmits image signals of the internal walls of the tubes in a coelom while passing through such a tube after being swallowed by a patient 2. An external unit 5 (one that is placed outside the patient's body) receives radio signals transmitted by this capsule endoscope 3 through an antenna unit 4 and stores the images.

In this external unit 5, a memory unit such as a compact flash memory of 1 gigabyte capacity, for example, is used to store the image data. The external unit 5 can then be connected to a display system 6 (FIG. 1(B)) in order to display images either during an examination or after the examination has been completed. The external unit 5 may be attached/detached to a personal computer 7 (hereinafter PC 7) using a communication cable, such as a USB cable 8. Images that are stored in the external unit can be transferred to the PC 7, where they may variously be processed for displaying, stored in a hard disk, and/or displayed. The keyboard 10 may be used for data input to the PC 7. As for the USB cable 8, any one of the communication standards USB 1.0, USB 1.1, and USB 2 can be used. Also, serial data communications can be used, such as the standards RS-232C and IEEE 1394.

When performing an endoscopic examination by swallowing a capsule endoscope 3 as shown in FIG. 1(A), an antenna unit 4 with multiple antennas 12 attached is used to receive the wireless image signals. The antennas are installed inside a shielding shirt 11 which provides an electromagnetic shielding function and is worn by a patient 2. The shielding shirt contains electrically conductive fibers which are electrically isolated from the antennas 12. Imaging is performed by the capsule endoscope 3 which transmits the images wirelessly, signals are received from the capsule endoscope using the antennas 12, and the images can then be temporarily stored in an external unit 5 which is connected to the antenna unit 4. The external unit 5 may be attached to the patient by a belt and, for example, a detachable hook. Also, the external unit 5 may be box-shaped, for example, with the front surface thereof provided with a liquid crystal monitor 13 for displaying images and an operating button 14 which controls the external unit 5. Inside the external unit 5 are provided a communication circuit, a control circuit, an image data display circuit, and a power supply.

Figure 2:
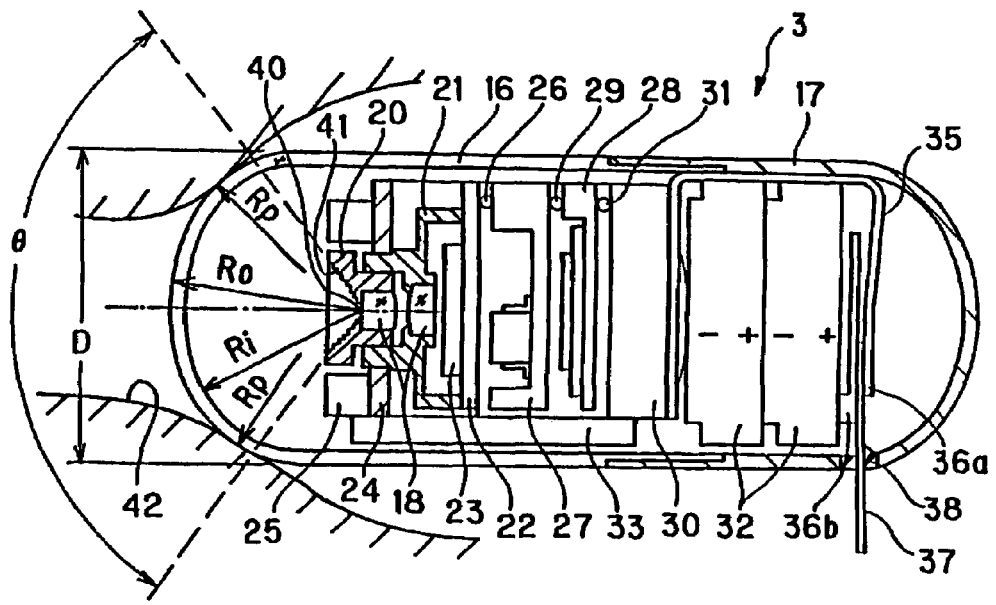
FIG. 2 is a cross-sectional view showing the internal configuration of a capsule endoscope according to Embodiment 1 of the invention.

As shown in FIG. 2, the capsule endoscope 3 may include a transparent front cover 16 that is formed as a cylinder having a transparent front end that includes regions having two different radii of curvature Rp, Ro for the outer surface, and a rear capsule portion 17 which mates with the transparent front cover so as to form a water-tight capsule that encloses an objective optical system 18.

Although not a preferred embodiment, the objective optical system 18 may be formed by attaching a first lens, in order from the object or front side, to a first lens frame 20 and a second lens to a second lens frame 21. The objective optical system 18 is then placed in a central position facing the front cover 16, and a CMOS image sensor 23 that is attached to the front surface of a circuit board 22 is placed at the image plane of the optical system 18. Also, at least one white LED 25 is attached to a front surface of a circuit board 24 that is supported, for example, by being fixed to the first lens frame 20.

A circuit board 22, to which the CMOS image sensor 23 is attached, is electrically connected by a connector 26 to a driving/processing circuit board 27 where electronic parts are mounted. Also, on a surface of a circuit board rearward of this driving/processing circuit board 27, a memory circuit 28 may be mounted for storing image data. The memory circuit 28 may be electrically connected by a connector 29. Rearward of the memory circuit 28, a wireless communication circuit 30 may be provided and electrically connected via a connector 31. Furthermore, rearward of the circuit board that supports the wireless communication circuit 30, two button-type batteries 32 may be provided. On the side neighboring the circuit board where the driving/processing circuit 27 is formed, an antenna 33 is provided and is connected with the wireless communication circuit 30. A battery 32 has its negative electrode connected to the ground of the wireless communication circuit 30, and the other end is connected via a spring-shaped contact element 35 so as to be the power supply of the wireless communication circuit 30. The spring-shaped contact element 35 serves as a contact section 36a on the positive side of the battery 32, and another contact section 36b is connected to the positive electrode of the battery 32. Neighboring the contact section 36a, an insulating element 37 is ordinarily inserted so that the capsule endoscope is set to the OFF state.

A part of this insulating element 37 is exposed to the exterior through a small opening of an elastic valve section 38 installed on the rear cover 17, and the contact sections 36a and 36b come into contact so as to turn the capsule endoscope to the ON state by pulling out the insulating element 37. The elastic valve section 38 then seals closed so as to retain the capsule endoscope in a water-tight condition.

In the transparent front cover 16, the inner surface and the outer surface of the dome-shaped part facing the objective optical system 18 are set to have radii of curvature Ri and Ro, respectively, in a center region of the field of view. In this embodiment, Ri equals 6.0 mm and Ro equals 6.5 mm, for example. Thus, in this embodiment, the thickness of the front cover 16 is uniform within the center region of the field of view $\theta$. Also, the centers of curvature for both radii are on the optical axis at the entrance pupil 40 of the objective optical system 18. In the periphery region of the field of view, the curvature radius Rp of the outer surface is set to a value smaller than curvature radii Ri and Ro (more specifically Rp equals 4.0 mm) so that the transparent front cover connects to the capsule side wall smoothly. Thus, an outer surface of the transparent cover has a fixed radius of curvature in a central region of the field of view of the objective optical system that is larger than the radius of curvature in the peripheral region of the field of view, and an inner surface of the transparent cover has a fixed radius of curvature which is smaller than the radius of curvature of the outer surface in the central region and larger than the radius of curvature of the outer surface in the peripheral region. The outer diameter D of the capsule endoscope 3 in this embodiment equals 11 mm. By making the cone-shaped, front surface of the first lens frame 20 be a rough surface 41, an antireflection function is provided by this surface. The center region of the field of view in this embodiment subtends an angle in the range of about 90°-110°.

The capsule endoscope 3 of this embodiment has the following characteristics. When the capsule endoscope 3 is swallowed, the periphery region of the front cover 16 of the capsule endoscope 3 comes into contact with mucosa 42 of organ lumens more easily than does the central region of the front cover. Referring to FIG. 2, because the radius of curvature Ro in the central region is large, and because the radius of curvature Rp at the periphery is small, the front periphery of the capsule endoscope comes into contact with the mucosa 42, and the central region within the periphery does not come into contact with the mucosa layer. By this, a state that allows sufficient field of view for observations can be assured. Also, if Rp (the radius of curvature in the periphery region of the field of view) were to have nearly as large a radius of curvature as Ro (the radius of curvature in the central region of the field of view), the outer diameter of the capsule would necessarily be larger, making the capsule difficult to swallow and reducing its mobility within the body after being swallowed. By making the capsule endoscope small, ease of swallowing as well as the mobility of the capsule within the body is improved. For example, if Rp is smaller than Ro, the outer diameter D (FIG. 2) can be made smaller than two times Ro. Thus, if Ro equals 5.5 mm, D can be made smaller than 11.0 mm. On the other hand, if the Rp is given the same curvature as Ro, the outer diameter D becomes 13 mm.

Also, by making the radius of curvature of the central region larger than the radius of curvature at the periphery (an example which best illustrates this situation is if the radius of curvature of the central region is made infinite), the amount of projection of the central section can be suppressed, the overall length of the capsule can be shortened, and the ease of swallowing can be improved. Therefore, the present embodiment allows both the outer diameter and the overall length of the capsule to be reduced, resulting in the capsule being easier to swallow and providing a wider field of view.

EMBODIMENT 2

Figure 3:
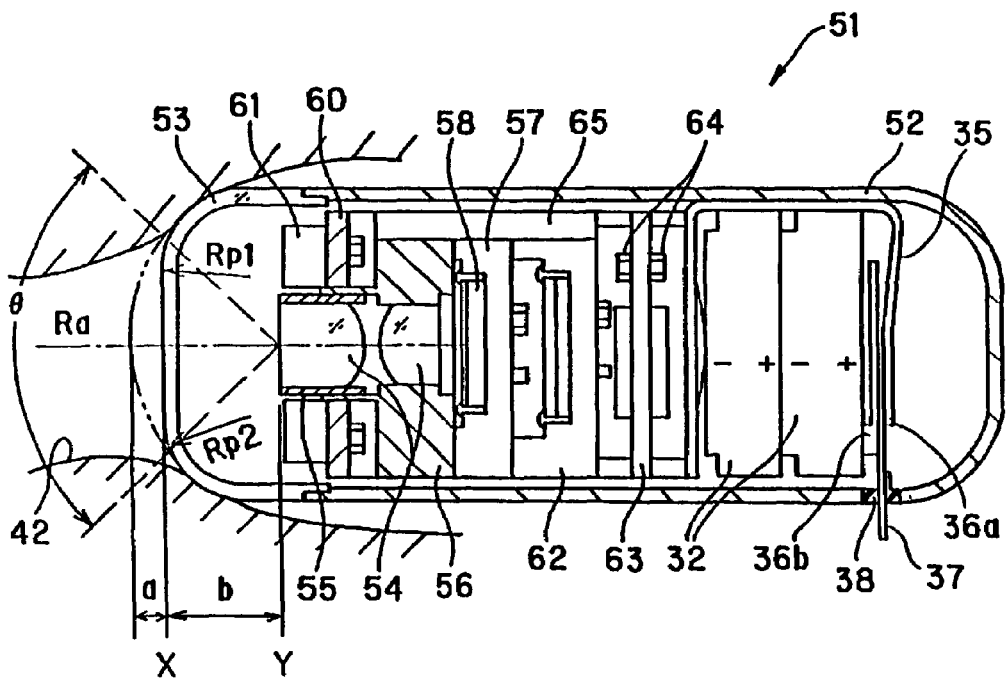
FIG. 3 is a cross-sectional view showing the internal configuration of a capsule endoscope according to Embodiment 2 of the invention.

FIG. 3 is a cross-sectional view showing the internal configuration of a capsule endoscope 51 according to Embodiment 2 of the invention. In the capsule endoscope 51, a transparent front cover 53 is fitted and glued to the front end of a member 52 which has a cylindrical shape. The rear end of the capsule endoscope 51 is closed using a rounded shape, making the interior of the capsule endoscope 51 watertight. An objective optical system 54 is provided within the capsule endoscope. Behind a central region of the transparent cover 53, the objective optical system 54 is formed by attaching a first lens to the first lens frame 55 and a second lens to a second lens frame 56, respectively. At the image plane, a CMOS image sensor 58 is installed on a planar surface that forms the lower surface of a two-level recessed portion at a front surface of a circuit board 57. Nearer the front of the capsule, a circuit board 60 is matched and glued to a cylindrical section of the second lens frame 56 which matches with the first lens frame 55, and multiple LED's 61 which emit white light are then attached to the front surface of the circuit board. On the back surface of the circuit board 57 to which the CMOS image sensor 58 is attached, a driving/processing and memory circuit 62 is placed. Behind this, a circuit board constituting a wireless communication circuit 63 is placed. On both sides of this circuit board, electronic chips 64, etc., may be mounted. Rearward of the wireless communication circuit 63, two button-type batteries 32 are placed. On a side section neighboring the circuit board that forms the driving/processing circuit 62, an antenna 65 is placed and is connected to the wireless communication circuit 63. Rearward of the wireless communication circuit 63, batteries 32 are connected to a spring-shaped contact element 35 as in the first embodiment explained in FIG. 2. An insulating element 37 is inserted so as to maintain the capsule endoscope in the OFF state, until such time as the insulating element 37 is pulled out so that contact sections 36a and 36b come into contact and power the capsule endoscope in ON state. As before, an elastic valve section 38 closes to retain water-tightness of the capsule endoscope when the insulating element 37 is pulled out.

Referring to FIG. 3, the inner surface and the outer surface of a central region of the field of view of the transparent front cover 53 of this embodiment have a nearly planar shape (i.e., the radius of curvature is large), with the field of view θ being in the range from about 90°-110°, for example. Peripheral to this region (termed the periphery region), the radii of curvature Rp1 and Rp2 are illustrated. However, it should be kept in mind that this drawing is a side-sectional view, and thus Rp1 and Rp2 are actually a single radius of curvature of the periphery region about a circle which is centered about the optical axis. The tails of the arrows Rp1 and Rp2 that are shown in FIG. 3 originate on this circle, which otherwise is not illustrated in the drawing figure. In this manner the transparent front cover is made to smoothly connect to the cylindrical side section of the capsule, with Rp1 and Rp2 being in the range of 1 mm-5 mm, for example. The thickness of the transparent cover 53 in the periphery region is made uniform in this embodiment as well. As before, the field of view of the optical system is indicated by θ. However, in this embodiment, as indicated by a curved two-dot line of radius of curvature Ra, objects within this distance in the field of view θ are out of focus, and objects outside of this distance in the field of view θ are in focus. Referring to FIG. 3, if the optical axis position of the front surface of the first lens of the objective optical system 54 is denoted as Y, the optical axis position of the front surface of the transparent cover 53 is denoted as X, the distance between these points is denoted as b, and the distance from X to the optical axis position of the two-dot chain line (of radius of curvature Ra) is denoted as a, then the objects more distant than a+b from the front surface of the first lens of the objective optical system 54 are in focus, and objects within this distance are out of focus.

By making the central region of the field of view of the transparent cover 53 a planar shape, the amount of projection in the central region can be suppressed, and the total length of the capsule endoscope 51 can be shortened. Therefore, the ease of swallowing can be improved. Also, by making the central region of the field of view of the transparent cover 53 a planar shape, its becomes less likely that the central region will come into contact with the mucosa 42. Thus, the field of view can be secured. Furthermore, since the position of the outer surface of the transparent cover 53 becomes out of focus, this is helpful in that anything at the surface will not be well-defined in the image formed by the objective optical system 54. Furthermore, since the overall length of the capsule is shortened with this design of the transparent front cover, there is an advantage in that the total length of the capsule becomes shorter, making the capsule easier to swallow.

EMBODIMENT 3

Figure 4:
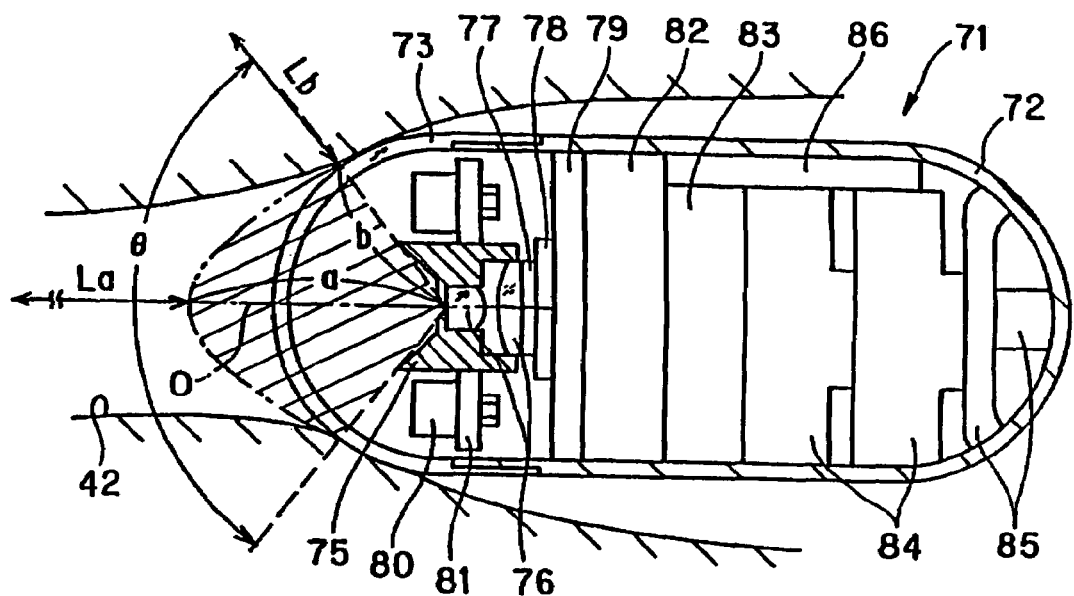
FIG. 4 is a cross-sectional view showing the internal configuration of a capsule endoscope according to Embodiment 3 of the invention.

FIG. 4 is a cross-sectional view showing the internal configuration of a capsule endoscope according to Embodiment 3 of the invention. In the capsule endoscope 71 shown in FIG. 4, a transparent cover 73 that includes a hemispheric-shaped front end is water-tightly fixed to the open end section of a rear case 72 which has a cylindrical shape. The rear case 72 has its other end closed by a rounded shape.

The following components are contained within the capsule endoscope 71. At an axial position facing the transparent cover 73, there is an objective optical system 76 which is attached to a lens frame 75. At the image surface of the objective optical system 76 is placed a CMOS image sensor 78 which is protected by a cover glass 77. This CMOS image sensor 78 is mounted to the front surface of a circuit board 79. Of course, instead of a CMOS image sensor 78, a CCD image sensor can instead be used.

The objective optical system 76 consists of two plano-convex lens elements. The planar rear surface of the second lens element is fixed in place by being adhesively attached to the cover glass 77. Then, a focus adjustment is performed wherein a lens frame 75 which has an inner diameter that matches with the outer diameter of the rear lens, is slid over the outer diameter of the rear lens in the direction of the optical axis O. When the image surface coincides with the detecting surface of the image sensor 78, the lens frame 75 is fixed to the rear lens using an adhesive.

At least one circuit board 81 with a white-light emitting LED 80 attached is fixed to the lens frame 75 by matching a hole therein to the lens frame 75. The at least one circuit board 81 has an electronic chip mounted thereon which includes a driving circuit that drives the LED 80 so as to flash intermittently.

Also, rearward of the circuit board 79, a circuit board having a driving/processing circuit 82 formed thereon is provided for the purpose of driving the CMOS image sensor 78 via the circuit board 79. The driving/processing circuit 82 also processes signals output from the image sensor 78.

Rearward of the driving/processing circuit 82, there is a circuit board 83 which functions to wirelessly transmit processed image signals. Rearward of the circuit board 83 there are button-type batteries 84. Rearward of the button-type batteries 84 and forward of the rear end of this capsule-shaped container there is a switch 85 that enables the power of the capsule endoscope to be turned on remotely, such as by using a magnet. Adjacent one side of the circuit board 83 and within the capsule there is an antenna 86.

In this embodiment, the optical properties of the objective optical system 76 are set as shown in FIG. 4. The near-point position of the depth of field of the objective optical system 76 is nearer at the periphery of the field of view than in the central region of the field of view. In FIG. 4, the field of view is indicated by θ. More specifically, the range from the surface of the first lens, in order from the object side, of the objective optical system 76 to the distance a is set to be out of focus in the direction along the optical axis O as shown in FIG. 4, and the range La is set to be in focus. Also, at the peripheral boundary of the field of view θ, the range from the surface of the first lens, in order from the object side, of the objective optical system to the distance b is set to be out of focus, and the range Lb is set to be in focus. In other words, the cross-hatched area in FIG. 4 that is bounded by the two dot chain line forward of the objective optical system 76 is set to be out of focus, with a being the near point of focus of the depth of field on the optical axis O and b being the near point of focus of the depth of field at the peripheral boundary of the field of view. Thus, a is greater than b. Still more specifically, in this embodiment a equals 10 mm, the range of La is from 10 mm to 40 mm, b equals 5.5 mm, and the range of Lb is from 5.5 mm to 20 mm.

Figure 5A:
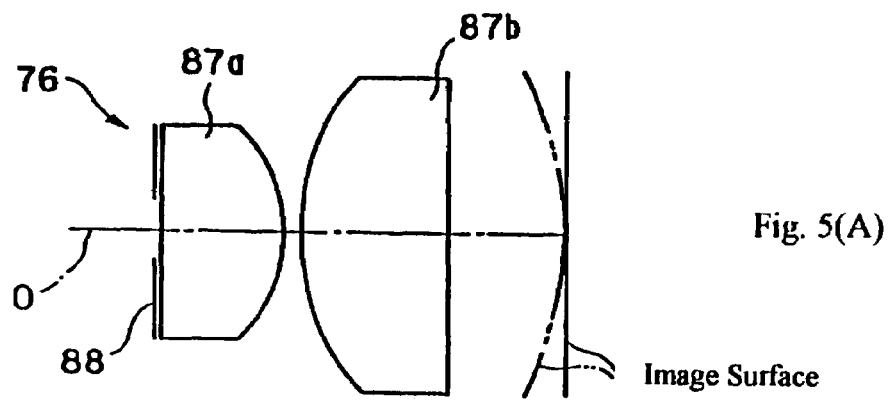
FIGS. 5(A) and 5(B) show different possible configurations of the objective optical system of a capsule endoscope.
Figure 5B:
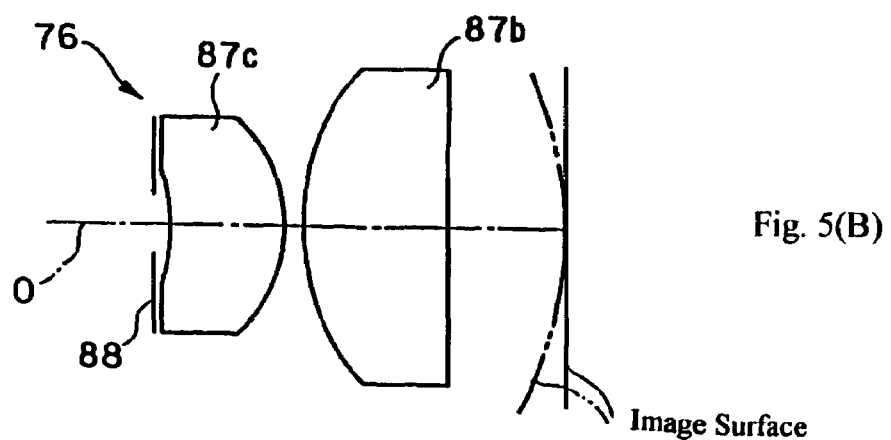

FIGS. 5(A) and 5(B) show different possible configurations of the objective optical system 76. In FIG. 5(A), the first lens and the second lens of the objective optical system 76 shown in FIG. 4 are each plano-convex lenses, with the planar surfaces facing the object and image sides, as illustrated. The first lens 87a has a smaller diameter than the second lens 87b, and an aperture stop 88 is before the first lens 87a as shown in FIG. 5(A). By forming the first lens 87a and the second lens 87b as illustrated, the image surface is curved, as illustrated by the two dot chain line in FIG. 5(A). In actuality, because the detecting surface of the image sensor chip is planar and perpendicular to the optical axis O, although the image of an object at an arbitrary distance coincides with the image surface near the optical axis O, at greater field angles the image is no longer formed on the detecting surface of the image sensor chip. Thus, although an object at an arbitrary distance is in focus in the center of the field of view, at larger field angles objects nearer the objective optical system than this arbitrary distance are also in focus.

Figure 6A:
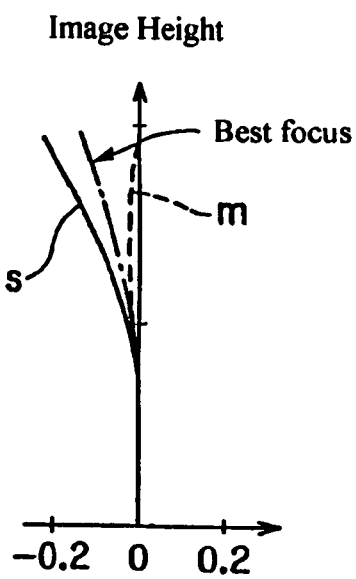
FIGS. 6(A) and 6(B) illustrate the astigmatism of the two objective optical systems shown in FIGS. 5(A) and 5(B), respectively.

FIG. 6(A) shows the astigmatism (for both the sagittal s, and meridional m image surfaces) in the case where the field of view is set to 90° in the objective optical system 76 shown in FIG. 5(A). In FIG. 6(A), zero on the abscissa indicates the image position for paraxial rays, with positions nearer the object side being indicated with a negative sign and the units being in mm. The ordinate is the image height. The curve shown in a dot-chain line between the s and m image surfaces is the position of best focus. In the case of the optical system shown in FIG. 5(A), the astigmatism rapidly increases when the field of view exceeds 90°. Thus, where larger fields of view are desired, it is desirable to design the optical system as shown in FIG. 5(B), wherein the first lens 87c has a positive meniscus shape instead of being a plano-convex lens. This meniscus lens 87c has a concave front surface of a relatively large radius of curvature.

In conventional endoscopes, in the case where an imaging unit is inserted into a coelom and an operation unit which is outside the body is used to control the field of view direction of the imaging unit, because the field of view direction can be adjusted to a direction desired by the observer, observations can be made by adjusting the field of view so that an object of interest is located within the field of view. In such an imaging unit, the various aberrations are preferably corrected over the entire field of view.

On the other hand, in a capsule endoscope, it is difficult to control the field of view direction of the imaging unit. Because of this, it is desirable that a focused observation image be obtained whether the observation target is near the center of the field of view or in the peripheral part of the field of view. In the case of observing an inner wall region of an organ lumen, for example, the inner wall region is the target of observation, and this region is often located in the peripheral part of the field of view. Also, forward of the imaging unit, is a transparent cover having a curved surface. Because observations of interest are made at the periphery of the field of view, the central region of the field of view does not have to be in focus. With this in mind, in this embodiment, the objective optical system 76 is intentionally designed so that the periphery of the field of view is in focus for object distances adjacent the periphery of the transparent cover, and so that objects adjacent the transparent cover near the center of the field of view are out of focus. If the objective optical system 76 is constructed of two positive lens elements, the Petzval sum becomes large, and the image position in the peripheral region where the angle of view is large can be more toward the object side than is the paraxial image position. Because the image sensor surface is placed perpendicular to the optical axis O, if the image sensor surface is placed at the paraxial image position, the peripheral rays will be out of focus on the image sensor.

Figure 6B:
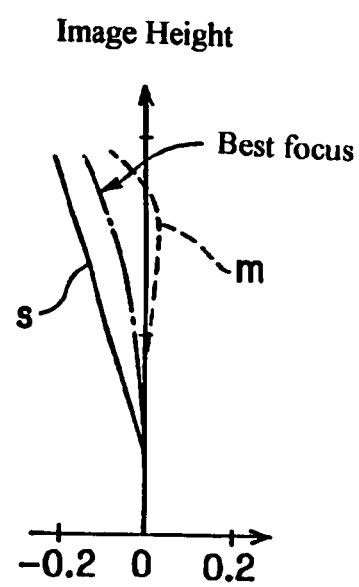

As shown in FIGS. 6(A) and 6(B), the sagittal image plane s lies more toward the object side (in the minus direction) than the meridional image plane m. As a result, the best image for both s and m rays is as illustrated, and is inclined toward the object side with increasing ray height. Also, in the capsule endoscope 71, it is preferred that the field of view of the objective optical system 76 be a wide-angle field of view so that the widest possible view field is obtained. In this case, the required field of view for the objective optical system 76 is from 90° to 140°. If such a wide-angle objective optical system 76 is formed of two plano-convex lens elements as in FIG. 5(A) above, the astigmatism as a function of image height (i.e., in the peripheral region of the field of view) rapidly increases, the best image inclines toward the object side with increasing field angle and thus the image quality degrades. In order to overcome these problems, an objective optical system 76 is provided that is formed of a positive meniscus lens 87c as shown in FIG. 5(B) in lieu of using a plano-convex lens as in FIG. 5(A).

FIG. 6(B) illustrates the astigmatism of the objective optical system shown in FIG. 5(B). The objective optical system 76 in FIG. 5(B) is characterized by the fact that the first lens element 87c has a concave surface on the object side in order to correct for astigmatism generated by the opposite convex surface of the lens element. In this manner, the inclination of the "best focus" curve of FIG. 6(B) toward the object side with increasing image height is controlled. The optimum configuration of an optical system for a capsule endoscope 71 is one that has an appropriate image surface curve while providing a wide-angle field of view without degradation of the image.

Although a meniscus lens is usually more expensive to produce than a plano-convex lens, for high volumes of production, the costs are reduced if the meniscus lens 87c is made of optical-grade plastic by injection molding. In fact, for high volumes of production the cost of the plano-convex lens 87b is less if made of optical-grade plastic by injection molding.

EMBODIMENT 4

Figure 7:
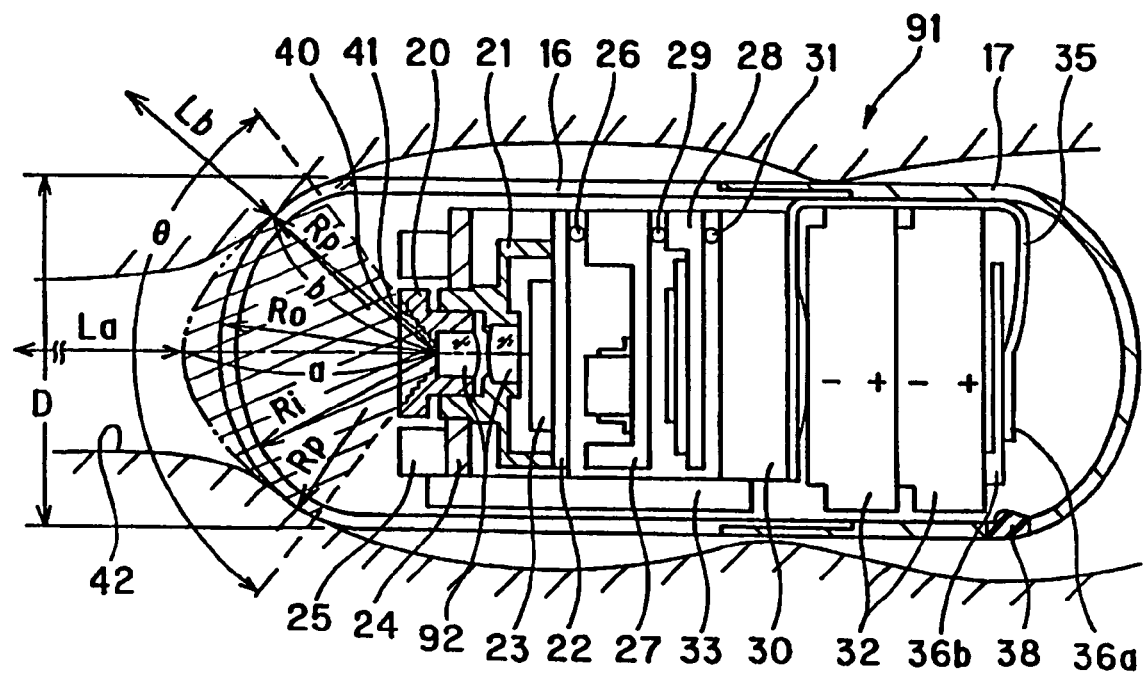
FIG. 7 is a cross-sectional view showing the internal configuration of a capsule endoscope according to Embodiment 4 of the invention.

FIG. 7 is a cross-sectional view showing the internal configuration of a capsule endoscope according to Embodiment 4 of the invention. The capsule endoscope 91 of this embodiment has almost the same configuration as that of Embodiment 1. However, instead of using the objective optical system 18, an objective optical system 92 is used that is similar to the objective optical system of Embodiment 3. Just as in Embodiment 3, the objective optical system has a different depth of field in the central region of the field of view versus the peripheral region of the field of view. The near-point position of the depth of field of the objective optical system 76 is nearer at the periphery of the field of view than in the central region of the field of view. More specifically, in this embodiment a=8 mm, La=8 mm to 30 mm, b=6 mm, and Lb=6 mm to 25 mm. The cross-hatched area in FIG. 7 that is bounded by the two dot chain line forward of the objective optical system 92 is set to be out of focus.

In this embodiment, the inner surface and outer surface which form the transparent front cover 16 have a constant radii of curvature Ri and Ro, respectively, up to near the periphery of the field of view range θ. In this embodiment, Ri equals 6.0 mm and Ro equals 6.5 mm, for example. Also, the transparent front cover at the outer boundary of the field of view connects smoothly with the side wall of the capsule by having the radius of curvature of the transparent front cover in the periphery region Rp equal 4 mm, for example. This embodiment has similar advantages as that of Embodiment 3.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. A capsule endoscope comprising:
   an illumination source;
   an imaging system that includes an objective optical system; and
   a transparent cover which has a larger fixed radius of curvature within an area in a central region of the field of view of the objective optical system than the radius of curvature of the transparent cover in a peripheral region of the field of view.

2. The capsule endoscope as set forth in claim 1, and further comprising:
   an image sensor; and
   a transmitter which transmits electromagnetic signals containing data output by the image sensor.

3. The capsule endoscope as set forth in claim 1, wherein the transparent cover includes a central region of the field of view that is planar, and the transparent cover satisfies the following condition in a peripheral region of the field of view $1 \leq r \leq 5$ where r is the radius of curvature of a surface of the transparent cover, in mm.

4. The capsule endoscope as set forth in claim 1, wherein a central region of the field of view of the objective optical system has a different depth of field than the field of view of the objective optical system outside the central region.

5. The capsule endoscope as set forth in claim 4, wherein the near point position of the depth of field of the objective optical system within the central region is larger than the near point position of the depth of field of the objective optical system outside the central region.

6. The capsule endoscope as set forth in claim 1, wherein:
   an outer surface of the transparent cover has a fixed radius of curvature in a central region of the field of view of the objective optical system that is larger than the radius of curvature in the peripheral region of the field of view, and
   an inner surface of the transparent cover has a fixed radius of curvature that is smaller than the radius of curvature of the outer surface in the central region and larger than the radius of curvature of the outer surface in the peripheral region.

* * * * *